(12) United States Patent
Kelly

(10) Patent No.: US 10,004,868 B2
(45) Date of Patent: Jun. 26, 2018

(54) BYPASS FLOW ELEMENT FOR DIVERTER FLOW MEASUREMENT

(75) Inventor: Eamonn Kelly, Carlsbad, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1210 days.

(21) Appl. No.: 13/257,705

(22) PCT Filed: Mar. 10, 2010

(86) PCT No.: PCT/IB2010/051040
§ 371 (c)(1),
(2), (4) Date: Sep. 20, 2011

(87) PCT Pub. No.: WO2010/109362
PCT Pub. Date: Sep. 30, 2010

(65) Prior Publication Data
US 2012/0006325 A1    Jan. 12, 2012

Related U.S. Application Data

(60) Provisional application No. 61/162,479, filed on Mar. 23, 2009.

(51) Int. Cl.
*A61M 16/08* (2006.01)
*A61M 16/00* (2006.01)
*A61M 16/12* (2006.01)

(52) U.S. Cl.
CPC ...... *A61M 16/085* (2014.02); *A61M 16/0003* (2014.02); *A61M 16/0841* (2014.02); *A61M 16/12* (2013.01); *A61M 2016/003* (2013.01); *A61M 2016/0039* (2013.01); *A61M 2202/0208* (2013.01)

(58) Field of Classification Search
CPC .. A61M 16/12; A61M 16/0003; A61M 16/00; A61M 16/0841; A61M 16/085; A61M 16/10; A61M 16/1005; A61M 2016/003; A61M 2016/0033; A61M 2016/0036; A61M 2016/0039; A61M 2016/0042; A61M 2202/0208; A61M 2206/10; A61M 2206/11
USPC ............ 128/205.11, 203.25, 204.18, 204.22; 138/38, 39, 31, 46
See application file for complete search history.

(56) References Cited

U.S. PATENT DOCUMENTS

| | | | |
|---|---|---|---|
| 3,838,598 A * | 10/1974 | Tompkins | G01F 1/42 73/861.52 |
| 4,118,973 A | 10/1978 | Tucker | |
| 6,601,460 B1 | 8/2003 | Materna | |
| 7,224,285 B2 * | 5/2007 | Tiwet et al. | 340/632 |
| 7,464,611 B2 * | 12/2008 | Matter | G01F 1/6842 73/202 |

(Continued)

FOREIGN PATENT DOCUMENTS

| JP | 2009500124 A | 1/2009 |
|---|---|---|
| RU | 34979 U1 | 12/2003 |

*Primary Examiner* — Colin W Stuart

(57) ABSTRACT

A ventilator includes a first pathway configured to supply a first gas; a second pathway configured to supply a second gas; a bypass element configured to provide a portion of the first gas and a portion of the second gas, the bypass element comprising a rib adjacent to a bypass conduit, wherein fluid flow is substantially laminar adjacent to the conduit. A bypass element is described.

14 Claims, 5 Drawing Sheets

(56) References Cited

U.S. PATENT DOCUMENTS

| | | | |
|---|---|---|---|
| 2003/0106554 A1* | 6/2003 | de Silva | A61M 16/12 128/204.22 |
| 2005/0039809 A1 | 2/2005 | Speldrich | |
| 2007/0044799 A1 | 3/2007 | Hete | |
| 2007/0062529 A1* | 3/2007 | Choncholas et al. | 128/204.22 |
| 2008/0078386 A1* | 4/2008 | Feldhahn | A61M 16/06 128/204.18 |

* cited by examiner

BYPASS FLOW ELEMENT FOR DIVERTER FLOW MEASUREMENT

BACKGROUND AND SUMMARY

A ventilator delivers a flow of pressurized gas, such as air and/or a mixture of air and extra (supplemental) oxygen, to the airway of a patient in order to assist in or substitute for the patient's breathing. A ventilator operates cyclically, such that the gas is provided to the patient during an inspiratory phase (corresponding to inhalation) and received from the patient during a subsequent expiratory phase (corresponding to exhalation). In order to provide a mixture of air and extra oxygen, for example, the ventilator receives air through an air pathway and pure oxygen through a separate oxygen pathway, and thus controls respective levels of each gas to obtain the desired mixture, provided to the patient during the inspiratory phase.

Generally, the patient interacts with a ventilator through conduits or "limbs," which conduct gas flow. A single limb ventilator provides a single conduit for inspiratory and expiratory phases, meaning that the patient receives (pressurized) gas from the ventilator during inhalation and discharges gas to the ventilator during exhalation through the same conduit. Typically, the discharged gas is directed through the air pathway of the ventilator. When the inspiratory gas flow includes a mixture of air and oxygen, for example, the expiratory gas flow necessarily includes at least a portion of the extra oxygen, resulting in "oxygen contamination" in the air pathway. Therefore, during the subsequent cycle of the inspiratory gas flow, the gas from the air pathway includes a higher concentration of oxygen than pure air. When the gas from the air pathway is mixed with additional oxygen from the oxygen pathway, the mixed gas provided to the patient has a higher than desired concentration of oxygen.

In order to ensure that the proper mixture of air and oxygen are provided, a sample of the mixture is taken. Because of limitations of known flow meters used in the determination of the mixture, the flow rate or flow volume of the sample is generally much smaller than that of the ventilator. Presenting the sample can be problematic, particularly in view of the limitations of the flow sensors and volume sensors. Moreover, sensing the oxygen and air in both inspiration and expiration can cause obstructions and compromised flow.

In one aspect, a ventilator includes a first pathway configured to supply a first gas; a second pathway configured to supply a second gas; a bypass element configured to provide a portion of the first gas and a portion of the second gas, the bypass element comprising a rib adjacent to a bypass conduit, wherein fluid flow is substantially laminar adjacent to the conduit.

In another aspect, a bypass element configured to direct a first gas and a second gas from a ventilator, the bypass element comprising: a rib adjacent to a bypass conduit, wherein fluid flow is substantially laminar adjacent to the conduit.

DETAILED DESCRIPTION

In the following detailed description, for purposes of explanation and not limitation, example embodiments disclosing specific details are set forth in order to provide a thorough understanding of an embodiment according to the present teachings. However, it will be apparent to one having ordinary skill in the art having had the benefit of the present disclosure that other embodiments according to the present teachings that depart from the specific details disclosed herein remain within the scope of the appended claims. Moreover, descriptions of well-known devices and methods may be omitted so as to not obscure the description of the example embodiments. Such methods and devices are clearly within the scope of the present teachings.

Figure 1:
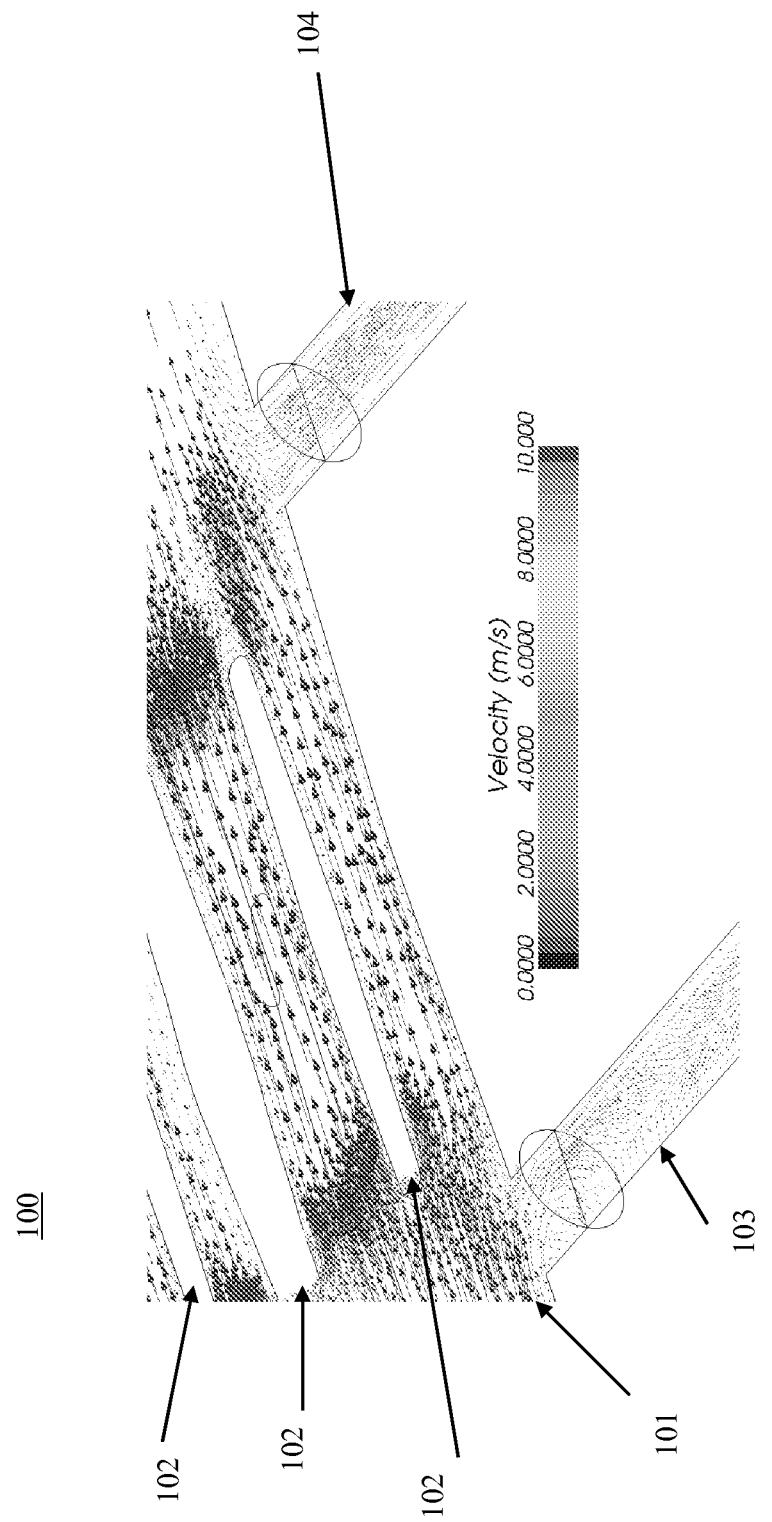
FIG. 1 is a conceptual view of a portion of a ventilator, according to a representative embodiment.

FIG. 1 is a conceptual view of a portion of a ventilator, according to a representative embodiment. The portion of the ventilator shown comprises air or oxygen flow 101 about a plurality of ribs within the conduits of the ventilator. As shown, the air (or oxygen) is diverted via a bypass conduit 103 to a flow-meter or volume-meter (not shown), and because the ventilator is a closed-system, the air (or oxygen) is returned by a bypass return 104. Notably, and as will become clearer as the present description continues, bypass conduits and returns are provided for both the air and oxygen of the ventilator so that the flow rates or flow volumes may be measured.

The ventilator measures air flow in the range of approximately −240 to approximately +240 SLPM (Standard Liters per Minute) and O2 flow in the range of approximately 0 SLPM to approximately 240 SLPM. In a representative embodiment, the flow measurement is part of the gas delivery assembly. The bypass element with ribs 102 overcomes issues of fill for injection molded parts. Beneficially, the geometry improves the fill and reduces the pressure required in an injection molding process. The area close to side-wall and flow diversion has been kept to a size to reduce turbulence as the flow in this area is close to a laminar flow Reynolds number. Stated somewhat differently, the Reynolds number is in the range of laminar flow.

Usefully, the ribs 102 are substantially straight ribs and are angled to the direction of the flow of plastic from the injection gate. Notably, the angle ensures the ribs 102 do not cut across the path of the bypass holes (interface between the bypass element 100 and the bypass conduit 103 and the bypass return 104), which could cause flow noise. There is no step at the points where the flow diverts; this reduces the possibility of substantial recirculation, which could cause flow noise on the signal from the mass flow sensor.

Notably, the ribs 102 provide a low pressure drop so that while the air or oxygen flow 101 is at a comparatively high pressure, the flow of air or oxygen in the bypass conduit 103 after the ribs 102 is comparatively low (e.g., less than 2.5 cm $H_2O$). As discussed above, the bypass element 100 is used with the mass flow sensor (not shown) to measure the flow range of the delivered gases. The mass flow sensor has a measurement ranger on the order of approximately 0 LPM to approximately ±1 LPM. The bypass element 100 thus diverts portion of the main flow across the mass flow sensor. The bypass conduit 102 has been sized to so that when the main flow is ±240 SLPM the diverted flow does not exceed the plus or minus 1 liter per minute range of the mass flow sensor. The mass flow sensor is calibrated with the bypass as described below in connection with FIGS. 5 and 6.

Figure 2:
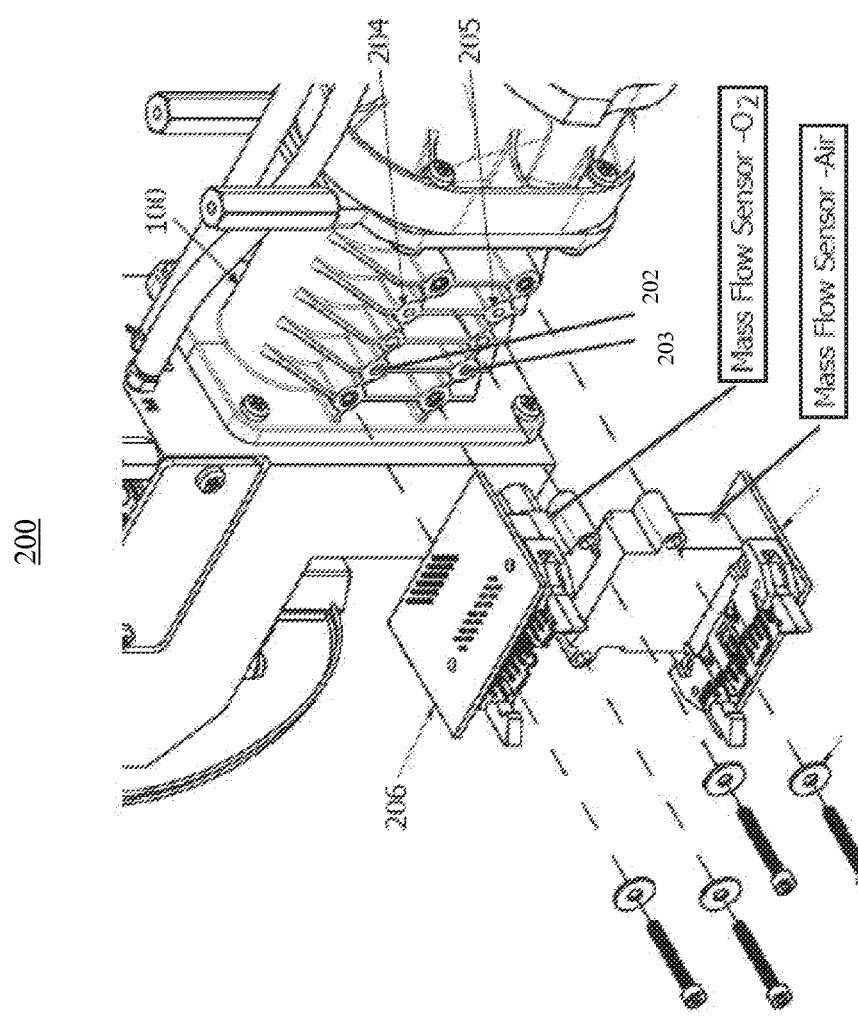
FIG. 2 is a perspective view of a ventilator including a bypass element, according to a representative embodiment.

FIG. 2 is a perspective view (with certain parts in exploded view) of a ventilator 200 including a bypass element 100, according to a representative embodiment. Many aspects of the ventilator are known, and as such many details thereof are not described to avoid obscuring the features of the bypass element 100 of the representative embodiments.

The bypass element 100 is provided along the regions of air and oxygen flow of the ventilator, and comprises conduits for bypassing oxygen and air to a flow sensor 206 and returning the bypass oxygen and air from the flow sensor 206. As shown, the flow sensor comprises an oxygen flow sensor and an air flow sensor.

The bypass element 100 comprises an oxygen bypass conduit 202 and an air bypass conduit 203. The bypass element further comprises an oxygen bypass return 204 and an air bypass return 205. The bypass element 100 further comprises ribs (not shown in FIG. 2) that maintain substantially laminar flow (i.e., Reynolds number comparatively low). Air and oxygen follow respective circuitous routes from the outlets of conduits 202, 203, through respective sensors of the flow sensor 206 and back to the element 100. The oxygen is provided to an inlet of an oxygen bypass return 204 and the air is provided to an inlet of an air bypass return 205, and thus back into the ventilator 200.

Figure 3:
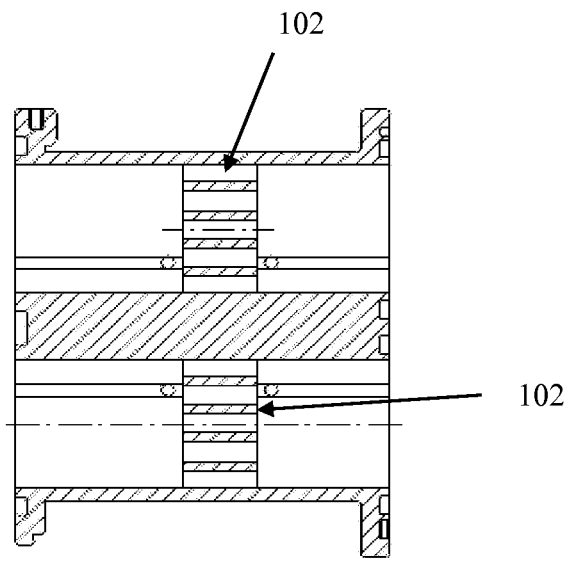
FIG. 3 is a cross-sectional view of a bypass element, according to a representative embodiment.

FIG. 3 is a cross-sectional view of a portion of a ventilator, according to a representative embodiment. FIG. 3 illustrates the ribs 102 of the bypass element 100 in accordance with a representative embodiment from a side where a flow sensor may be attached.

Figure 4:
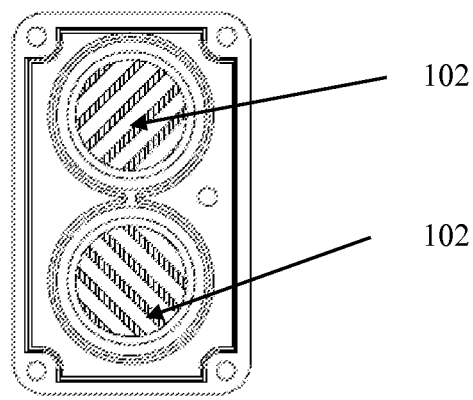
FIG. 4 is a cross-sectional view of a portion of a bypass element, according to a representative embodiment.

FIG. 4 is a cross-sectional view of a portion of a ventilator, according to a representative embodiment. FIG. 4 illustrates the ribs 102 of the bypass element 100 in accordance with a representative embodiment from an end view. Thus, airflow is into or out of the plane of the drawing plane.

Figure 5:
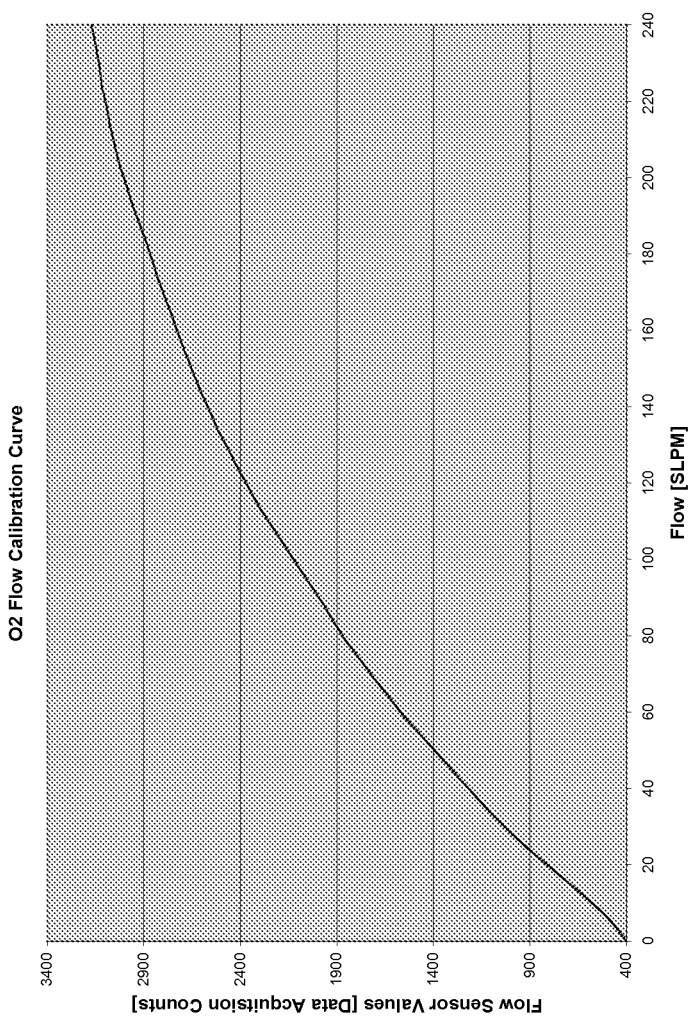
FIG. 5 is a graphical representation of a flow calibration curve in accordance with a representative embodiment.
Figure 6:
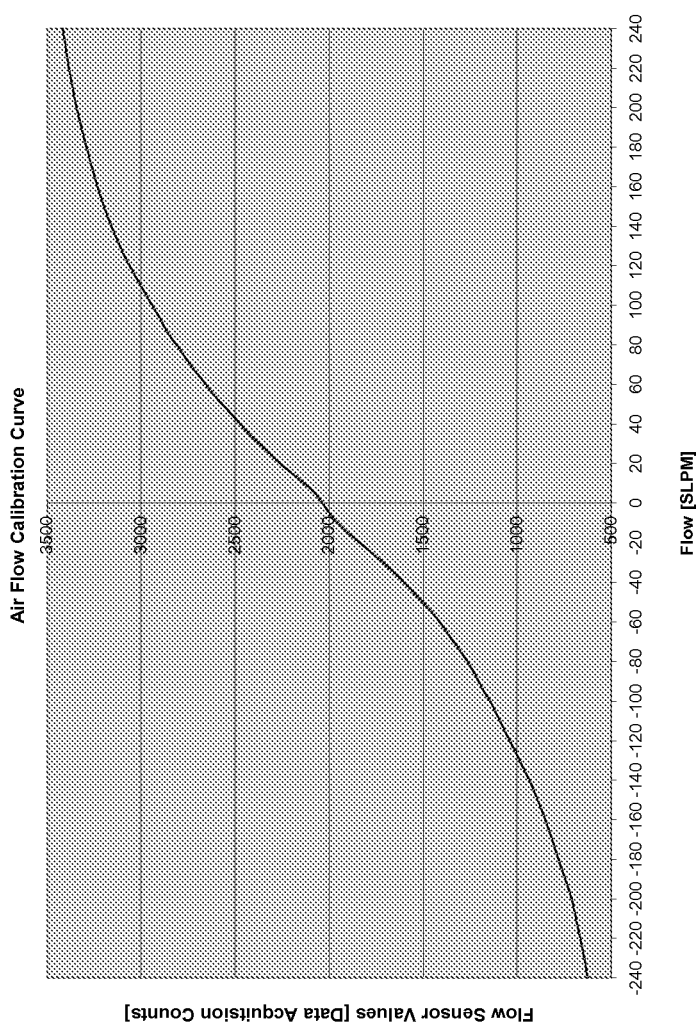
FIG. 6 is a graphical representation of a flow calibration curve in accordance with a representative embodiment.

FIGS. 5 and 6 are calibration curves useful in scaling the flow of oxygen and air, respectively, at a flow meter.

While preferred embodiments are disclosed herein, many variations are possible which remain within the concept and scope of the invention. Such variations would become clear to one of ordinary skill in the art after inspection of the specification, drawings and claims herein. The invention therefore is not to be restricted except within the spirit and scope of the appended claims.

What is claimed is:

1. A ventilator comprising:
a first pathway configured to supply a first gas;
a second pathway configured to supply a second gas; and
a bypass element configured to bypass a portion of the first gas through a first bypass conduit, and bypass a portion of the second gas through a second bypass conduit, the bypass element comprising a first rib adjacent to the first bypass conduit and a second rib adjacent to the second bypass conduit, wherein:
the bypass element is not tapered where each of the first and second bypass conduits bypass the portion of the respective first and second gasses,
the first rib provides a geometric chord with an inner perimeter of the first pathway when viewed from a perspective of a cross-section of the first pathway
the first rib divides first unobstructed sections of the first pathway, the second rib provides a geometric chord with an inner perimeter of the second pathway when viewed from a perspective of a cross-section of the second pathway, and
the second rib divides second unobstructed sections of the second pathway.

2. The ventilator of claim 1, wherein the first gas comprises air and the second gas comprises oxygen.

3. The ventilator of claim 1, wherein the bypass element is in fluid communication with a flow sensor or a volume sensor.

4. The ventilator of claim 3, wherein the first gas comprises air and the second gas comprises oxygen, the second bypass conduit is configured to carry oxygen from the ventilator, and the first bypass conduit is configured to carry air from the ventilator.

5. The ventilator of claim 1, further comprising a plurality of ribs adjacent to the first bypass conduit and another plurality of ribs adjacent to the second bypass conduit.

6. The ventilator of claim 1, wherein:
flow of the first gas in the first bypass conduit is less than 2.5 cm $H_2O$, and
flow of the second gas in the second bypass conduit is less than 2.5 cm $H_2O$.

7. The ventilator of claim 1, wherein flow of the first gas through the first bypass conduit does not exceed ±1 LPM when the flow of the first gas through the first pathway is between ±240 SLPM.

8. A bypass element configured to direct a first gas and a second gas from a ventilator, the bypass element comprising:
a first pathway that conveys the first gas; and
a first bypass conduit and a first bypass return that are in fluid communication with the first pathway, the first bypass conduit and first bypass return cooperate to bypass a portion of the first gas around a portion of the first pathway in which a first rib extends lengthwise within the first pathway between the first bypass conduit and the first bypass return, wherein:
the first pathway is not tapered where the first bypass conduit bypasses the portion of the first gas,
the first rib provides a geometric chord with an inner perimeter of the first pathway when viewed from a perspective of a cross-section of the first pathway, and
the first rib divides unobstructed sections of the first pathway.

9. The bypass element of claim 8, wherein the first gas comprises air.

10. The bypass element of claim 8, wherein the bypass element is in fluid communication with a flow sensor or a volume sensor.

11. The bypass element of claim 8, further comprising:
a second pathway that conveys the second gas; and
a second bypass conduit and a second bypass return that are in fluid communication with the second pathway, the second bypass conduit and second bypass return cooperate to bypass a portion of the second gas around a portion of the second pathway in which a second rib extends lengthwise within the second pathway between the second bypass conduit and the second bypass return, wherein
the first gas comprises air and the second gas comprises oxygen, the second bypass conduit is configured to carry oxygen, and the first bypass conduit is configured to carry air.

12. The bypass element of claim 11, further comprising a plurality of ribs adjacent to the first bypass conduit and another plurality of ribs adjacent to the second bypass conduit.

13. A bypass element of a ventilator, the bypass element comprising:
- a pathway that conveys a gas; and
- a bypass conduit and a bypass return that are in fluid communication with the pathway, the bypass conduit and bypass return cooperate to bypass a portion of the gas around a portion of the pathway in which a plurality of ribs extend lengthwise within the pathway substantially an entire distance between the bypass conduit and the bypass return but do not overlap either the bypass conduit or the bypass return, wherein:
- the pathway is not tapered where the bypass conduit bypasses the portion of the gas,
- each of the plurality of ribs provides a geometric chord with an inner perimeter of the pathway when viewed from a perspective of a cross-section of the pathway, and
- each of the plurality of ribs divides respective unobstructed sections of the pathway.

14. The bypass element of claim 13, wherein each of the plurality of ribs provides a geometric chord with the inner perimeter of the pathway when viewed from each of opposite perspectives of a cross-section of the pathway taken midway along the pathway between the bypass conduit and the bypass return.

* * * * *